(12) United States Patent
She et al.

(10) Patent No.: US 10,245,342 B2
(45) Date of Patent: Apr. 2, 2019

(54) ANTIMICROBIAL DEVICES FOR USE WITH MEDICAL DEVICES AND RELATED ASSEMBLIES AND METHODS

(71) Applicant: Health Line International Corp., Salt Lake City, UT (US)

(72) Inventors: Li Min She, Guangdong (CN); Joel K. Faulkner, Salt Lake City, UT (US); Zhao Jie, Beijing (CN); Aaron Garcia Faulkner, Salt Lake City, UT (US)

(73) Assignee: Health Line International Corp., Salt Lake City, UT (US)

(*) Notice: Subject to any disclaimer, the term of this patent is extended or adjusted under 35 U.S.C. 154(b) by 161 days.

(21) Appl. No.: 14/559,746

(22) Filed: Dec. 3, 2014

(65) Prior Publication Data

US 2015/0086441 A1    Mar. 26, 2015

Related U.S. Application Data

(63) Continuation of application No. PCT/US2014/000128, filed on May 14, 2014, and a continuation-in-part of application No. PCT/US2013/047154, filed on Jun. 21, 2013.

(60) Provisional application No. 61/663,287, filed on Jun. 22, 2012, provisional application No. 61/663,272, filed on Jun. 22, 2012.

(51) Int. Cl.
*A61L 2/18* (2006.01)
*A61M 39/16* (2006.01)
*A61M 39/20* (2006.01)

(52) U.S. Cl.
CPC ............. *A61L 2/18* (2013.01); *A61L 2202/24* (2013.01)

(58) Field of Classification Search
CPC .................................. A61L 2/18; A61M 39/16
USPC ........................................................... 422/294
See application file for complete search history.

(56) References Cited

U.S. PATENT DOCUMENTS

| | | |
|---|---|---|
| 3,315,830 A | 4/1967 | Flynn |
| 3,987,930 A | 10/1976 | Fuson |
| 4,046,276 A * | 9/1977 | Winchell ............... A61M 1/02 |
| | | 215/250 |
| 4,354,490 A | 10/1982 | Rogers |

(Continued)

FOREIGN PATENT DOCUMENTS

| | | |
|---|---|---|
| CA | 2775213 A1 | 6/2013 |
| CN | 101801435 A | 8/2010 |

(Continued)

OTHER PUBLICATIONS

ASM International, Materials and Coatings for Medical Devices: Cardiovascular, 2009, ASM International, p. 2118.*

(Continued)

*Primary Examiner* — Kevin Joyner
*Assistant Examiner* — Holly M Mull
(74) *Attorney, Agent, or Firm* — TraskBritt (57) ABSTRACT

Antimicrobial devices for use with at least a portion of a medical device include at least one flexible portion configured to secure the antimicrobial device to the at least a portion of the medical device. Medical device assemblies include an access port and an antimicrobial device adapted to disinfect at least a portion of the access port. Methods of disinfecting a portion of a device include deforming a housing of the antimicrobial device to couple the antimicrobial device to the portion of the device.

20 Claims, 4 Drawing Sheets

(56) References Cited

U.S. PATENT DOCUMENTS

| | | |
|---|---|---|
| 4,440,207 A | 4/1984 | Genatempo et al. |
| 4,624,664 A | 11/1986 | Peluso et al. |
| 4,671,306 A | 6/1987 | Spector |
| 4,696,393 A | 9/1987 | Laipply |
| 4,778,447 A | 10/1988 | Velde et al. |
| 5,053,003 A | 10/1991 | Dadson et al. |
| 5,190,534 A | 3/1993 | Kendell |
| 5,242,425 A | 9/1993 | White et al. |
| 5,536,258 A | 7/1996 | Folden |
| 5,554,135 A | 9/1996 | Menyhay |
| 5,694,978 A | 12/1997 | Heilmann et al. |
| 5,792,120 A | 8/1998 | Menyhay |
| 5,807,345 A | 9/1998 | Grabenkort |
| 5,820,604 A | 10/1998 | Fox et al. |
| 5,954,957 A | 9/1999 | Chin et al. |
| 7,316,669 B2 | 1/2008 | Ranalletta |
| 7,708,714 B2 | 5/2010 | Connell et al. |
| 7,780,794 B2 | 8/2010 | Rogers et al. |
| 7,794,675 B2 | 9/2010 | Lynn |
| 7,857,793 B2 | 12/2010 | Raulerson et al. |
| 7,922,701 B2 | 4/2011 | Buchman |
| 7,985,302 B2 | 7/2011 | Rogers et al. |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,602 B2 | 7/2012 | Anderson et al. |
| 8,252,247 B2 | 8/2012 | Ferlic |
| 8,273,303 B2 | 9/2012 | Ferlic et al. |
| 8,361,408 B2 | 1/2013 | Lynn |
| 8,388,894 B2 | 3/2013 | Colantonio et al. |
| 8,480,968 B2 | 7/2013 | Lynn |
| 8,491,546 B2 | 7/2013 | Hoang et al. |
| 8,628,501 B2 | 1/2014 | Hadden |
| 8,740,864 B2 | 6/2014 | Hoang et al. |
| 8,777,504 B2 | 7/2014 | Shaw et al. |
| 2004/0004019 A1 | 1/2004 | Busch |
| 2004/0215148 A1 | 10/2004 | Hwang et al. |
| 2004/0258560 A1 | 12/2004 | Lake, Jr. et al. |
| 2005/0124970 A1 | 6/2005 | Kunin et al. |
| 2007/0112333 A1 | 5/2007 | Hoang et al. |
| 2007/0225635 A1 | 9/2007 | Lynn |
| 2007/0225660 A1 | 9/2007 | Lynn |
| 2007/0282280 A1 | 12/2007 | Tennican |
| 2008/0038167 A1 | 2/2008 | Lynn |
| 2008/0086091 A1 | 4/2008 | Anderson et al. |
| 2008/0177250 A1 | 7/2008 | Howlett et al. |
| 2008/0235888 A1 | 10/2008 | Vaillancourt et al. |
| 2009/0008393 A1 | 1/2009 | Howlett et al. |
| 2009/0062766 A1 | 3/2009 | Howlett et al. |
| 2009/0099529 A1 | 4/2009 | Anderson et al. |
| 2009/0137969 A1 | 5/2009 | Colantonio et al. |
| 2010/0000040 A1 | 1/2010 | Shaw et al. |
| 2010/0003067 A1 | 1/2010 | Shaw et al. |
| 2010/0047123 A1 | 2/2010 | Solomon et al. |
| 2010/0049170 A1 | 2/2010 | Solomon et al. |
| 2010/0050351 A1* | 3/2010 | Colantonio ............... A61L 2/18 15/104.93 |
| 2010/0064456 A1 | 3/2010 | Ferlic |
| 2010/0172794 A1 | 7/2010 | Ferlic et al. |
| 2010/0242993 A1 | 9/2010 | Hoang et al. |
| 2010/0306938 A1 | 12/2010 | Rogers et al. |
| 2011/0044850 A1 | 2/2011 | Solomon et al. |
| 2011/0054440 A1 | 3/2011 | Lewis |
| 2011/0064512 A1 | 3/2011 | Shaw et al. |
| 2011/0125104 A1 | 5/2011 | Lynn |
| 2011/0184382 A1 | 7/2011 | Cady |
| 2011/0217212 A1 | 9/2011 | Solomon et al. |
| 2011/0232020 A1 | 9/2011 | Rogers et al. |
| 2011/0265825 A1 | 11/2011 | Rogers et al. |
| 2011/0277788 A1 | 11/2011 | Rogers et al. |
| 2011/0290799 A1 | 12/2011 | Anderson et al. |
| 2011/0314619 A1 | 12/2011 | Schweikert |
| 2012/0016318 A1 | 1/2012 | Hoang et al. |
| 2012/0022469 A1 | 1/2012 | Alpert |
| 2012/0078203 A1* | 3/2012 | Gaube ................... A61M 39/16 604/288.03 |
| 2012/0109073 A1 | 5/2012 | Anderson et al. |
| 2012/0245531 A9 | 9/2012 | Anderson et al. |
| 2012/0283693 A1 | 11/2012 | Anderson et al. |
| 2012/0296284 A1 | 11/2012 | Anderson et al. |
| 2012/0302997 A1* | 11/2012 | Gardner ................ A61M 39/20 604/533 |
| 2012/0315201 A1 | 12/2012 | Ferlic et al. |
| 2013/0006194 A1 | 1/2013 | Anderson et al. |
| 2013/0023828 A1 | 1/2013 | Anderson et al. |
| 2013/0030414 A1 | 1/2013 | Gardner et al. |
| 2013/0035667 A1 | 2/2013 | Anderson et al. |
| 2013/0164189 A1 | 6/2013 | Hadden |
| 2013/0171030 A1* | 7/2013 | Ferlic .................... A61M 39/20 422/119 |
| 2013/0197485 A1 | 8/2013 | Gardner et al. |

FOREIGN PATENT DOCUMENTS

| | | |
|---|---|---|
| CN | 103191511 A | 7/2013 |
| EP | 2444117 A1 | 4/2012 |
| EP | 2606930 A1 | 6/2013 |
| WO | 2006019782 A2 | 2/2006 |
| WO | 2008140807 A1 | 11/2008 |
| WO | 2009002474 A1 | 12/2008 |
| WO | 2009136957 A1 | 11/2009 |
| WO | 2010002757 A1 | 1/2010 |
| WO | 2011120017 A1 | 9/2011 |
| WO | 2012067778 A1 | 5/2012 |
| WO | 2012162006 A1 | 11/2012 |
| WO | 2012162259 A2 | 11/2012 |
| WO | 2013066742 A1 | 5/2013 |
| WO | 2013192574 A1 | 12/2013 |

OTHER PUBLICATIONS

Koshal, Manufacturing engineer's reference book, 1993, Butterworth-Heinemann, 2/7.*

PCT International Search Report and Written Opinion, PCT/US2013/047154, dated Sep. 17, 2013.

PCT International Search Report and Written Opinion, PCT/US2014/000128, dated Feb. 5, 2015.

Extended European Search Report from European Patent Application No. 14891838.6, dated Nov. 20, 2017, 8 pages.

* cited by examiner

ANTIMICROBIAL DEVICES FOR USE WITH MEDICAL DEVICES AND RELATED ASSEMBLIES AND METHODS

CROSS-REFERENCE TO RELATED APPLICATIONS

This application is a continuation of co-pending International Patent Application PCT/US2014/000128, filed May 14, 2014, for "ANTIMICROBIAL DEVICES FOR USE WITH MEDICAL DEVICES AND RELATED ASSEMBLIES AND METHODS," designating the United States, the disclosure of which is hereby incorporated herein in its entirety by this reference. This application is also a continuation-in-part of co-pending International Patent Application PCT/US2013/047154, filed Jun. 21, 2013, for "ANTIMICROBIAL DEVICES FOR USE WITH MEDICAL DEVICES AND RELATED ASSEMBLIES AND METHODS," designating the United States, published in English as International Patent Publication WO 2013/192574 A1 on Dec. 27, 2013, which claims the benefit under Article 8 of the Patent Cooperation Treaty and under 35 U.S.C. § 119(e) to U.S. Provisional Patent Application Ser. No. 61/663,287, filed Jun. 22, 2012, for "ANTIMICROBIAL DEVICES FOR USE WITH MEDICAL DEVICES AND RELATED ASSEMBLIES AND METHODS" and U.S. Provisional Patent Application Ser. No. 61/663,272, filed Jun. 22, 2012, for "ANTIMICROBIAL DEVICES FOR USE WITH MEDICAL DEVICES AND RELATED ASSEMBLIES AND METHODS," the disclosure of each of which is hereby incorporated herein in its entirety by this reference.

TECHNICAL FIELD

The disclosure generally relates to antimicrobial devices for use with medical devices and related assemblies and methods. In particular, embodiments of the disclosure relate to antimicrobial devices having at least one flexible portion for use in disinfecting at least a portion of a medical device, such as, one or more portions of a medical device for delivering fluid to and/or sampling fluid from a subject.

BACKGROUND

In the medical field and, in particular, within the area of delivery of fluids to a subject and removal of fluids from a subject, a need exists to prevent the transmission of pathogens into or onto a subject from a potentially contaminated surface of a medical device. Such pathogens include microorganisms such as bacteria and viruses. For example, bloodstream infections, which may be caused by microorganisms that enter patients via intravascular catheters, are a significant cause of illness and excess medical costs and may result in serious infections or death.

Traditionally, cleaning a potentially contaminated surface of a medical device includes treating the surface with an alcohol swab. Such alcohol swabs include cotton gauze soaked in, e.g., isopropyl alcohol or ethanol. The swab is applied by a healthcare provider and wiped across surface of the medical device. As the alcohol applied by the pad evaporates, it destroys microorganisms. Impregnating medical devices, such as catheters, with various antimicrobial agents is another approach for reducing the chances of contamination of the medical device.

Other devices comprising a cap for cleaning a medical device include WIPO Publication No. WO 2013/192574 A1 to Faulkner et al., published Dec. 27, 2013, PCT Application No. PCT/US2013/047159 to Faulkner et al., filed Jun. 21, 2013, United States Patent Application Publication No. US 2007/0112333 to Hoang et al., published May 17, 2007; U.S. Pat. No. 7,780,794 to Rogers et al., issued Aug. 24, 2010; United States Patent Application Publication No. US 2011/0044850 to Solomon et al., published Feb. 24, 2011; United States Patent Application Publication No. US 2011/0217212 to Solomon et al., published Sep. 8, 2011; and United States Patent Application Publication No. US 2011/0232020 to Rogers et al. published Sep. 29, 2011, the disclosure of each of which is hereby incorporated herein in its entirety by this reference.

BRIEF SUMMARY

Described are antimicrobial devices and related assemblies and methods for disinfecting at least a portion of a medical device, such as, one or more portions of a medical device for at least one of delivering fluid to and sampling fluid from a subject (e.g., an intravenous (IV) device).

Disclosed is a device for use with at least a portion of a medical device. The device may include a flexible housing having a cavity formed therein and an amount of liquid substance (e.g., disinfectant, lubricant, or soap) disposed within the cavity where at least a portion of the flexible housing is configured to secure the flexible housing to a portion of the medical device.

In some embodiments, the device further includes at least one flexible protrusion extending at least partially into the cavity of the flexible housing where the at least one flexible protrusion is configured to secure the flexible housing to a portion of the medical device.

In some embodiments, the flexible housing is configured to elastically deform responsive to a force applied to the flexible housing by fingers of a user.

In some embodiments, at least one of the flexible housing and the at least one flexible protrusion are configured to elastically deform about the at least a portion of the medical device in order to secure the antimicrobial device to the at least a portion of the medical device.

Also disclosed is a device for use in disinfecting at least a portion of a medical device. The antimicrobial device will typically include a flexible housing formed from a flexible material. The flexible housing has a first open end forming an access port in the antimicrobial device to a cavity formed in the housing for receiving the at least portion of the medical device within the antimicrobial device, a second closed end opposing the first open end, and a longitudinal axis extending between the first open end and the second closed end. The antimicrobial device further includes an antimicrobial substance contained within the cavity in an amount sufficient to disinfect at least a portion of the medical device and at least one flexible protrusion extending around and into the cavity from an inner surface of the flexible housing in a direction perpendicular to the longitudinal axis of the flexible housing. The at least one flexible protrusion is configured to secure the antimicrobial device to the at least a portion of the medical device in a manner allowing for the antimicrobial substance to make surface contact with the at least a portion of the medical device.

Also disclosed is an antimicrobial device for use with at least a portion of a medical device. The antimicrobial device will typically include a flexible housing comprising a volume of antimicrobial substance and at least one flexible member configured to secure the flexible housing to each of a threaded portion of the medical device and a non-threaded portion of the medical device.

Also disclosed is an antimicrobial device for use in disinfecting at least a portion of a medical device. The antimicrobial device will typically include a housing comprising a first open end forming an access port in the antimicrobial device to a cavity formed in the housing for receiving the at least portion of the medical device within the antimicrobial device, a second closed end opposing the first open end, a longitudinal axis extending between the first open end and the second closed end, and a plurality of concentric protrusions positioned along the longitudinal axis of the housing. Each of the plurality of concentric protrusions extends around and into the cavity from an inner surface of the housing. The antimicrobial device further includes an antimicrobial substance contained within the cavity in an amount sufficient to disinfect at least a portion of the medical device where the plurality of concentric protrusions are configured to secure the housing to the at least a portion of the medical device in a manner allowing for the antimicrobial substance to make surface contact with the at least a portion of the medical device.

Also disclosed is an antimicrobial device for use in disinfecting at least a portion of a medical device. The antimicrobial device will typically include a housing, a cavity disposed within the housing, an antimicrobial substance contained within the cavity in an amount sufficient to disinfect at least a portion of the medical device, and a flexible member associated with the housing. The flexible member includes a lateral portion extending at least partially across the cavity to form an access port in the antimicrobial device to the cavity for receiving the portion of the medical device within the antimicrobial device where the flexible member is configured to secure the antimicrobial substance to a non-threaded portion of the medical device in a manner allowing for the antimicrobial substance to make surface contact with the portion of the medical device.

Also disclosed is an antimicrobial device for use in disinfecting at least a portion of a medical device. The antimicrobial device will typically include a housing comprising an amount of antimicrobial substance where the inner surface of the housing is free of helical threads formed thereon and a flexible member associated with the housing and configured to secure the housing to the at least a portion of the medical device.

Also disclosed is a medical device assembly including an access port configured to sample fluid from a subject and/or deliver fluid to a subject and an antimicrobial device adapted to disinfect at least a portion of the access port.

Further disclosed is a method of disinfecting a portion of a device with an antiseptic and/or disinfectant solution such as alcohol and/or ethanol. The method includes deforming a housing of the antimicrobial device comprising a plurality of protrusions on an inner surface of the housing to couple the antimicrobial device to the portion of the device, retaining the antimicrobial device on the portion of the device for a selected period of time with at least one protrusion of the plurality of protrusions, and removing the antimicrobial device from the portion of the device.

Further disclosed is another method of disinfecting a portion of a device. The method includes coupling an antimicrobial device to the portion of the device and engaging one of a threaded portion and a non-threaded portion of the device with a flexible portion of the antimicrobial device.

Yet further disclosed are methods of making and forming such antimicrobial devices.

DETAILED DESCRIPTION

In the following detailed description, reference is made to the accompanying drawings that depict, by way of illustration, specific embodiments in which the disclosure may be practiced. However, other embodiments may be utilized.

Generally, antimicrobial devices as described herein may be utilized to disinfect potentially contaminated surfaces of various devices (e.g., medical devices). Related assemblies and methods are also disclosed herein. Such antimicrobial devices may be configured as a cap having a volume of antimicrobial substance therein. For example, the volume of antimicrobial substance may comprise a disinfectant and/or antiseptic (e.g., a disinfectant and/or antiseptic in a fluid state) such as, for example, alcohol (e.g., isopropyl alcohol) at various concentrations (e.g., 50 to 90%), ethanol at various concentrations (e.g., ranging from 50 to 95%), and combinations of these and any other suitable disinfectant and/or antiseptics. The cap may be coupled to and used to protect (e.g., by covering a portion of the medical device) and/or disinfect a portion of medical device by receiving the portion of the medical device (e.g., at least temporarily) within the cap.

In some embodiments, such antimicrobial devices reduce the likelihood of microorganisms entering the bloodstream of a subject via a medical device or assembly configured to deliver fluid to a subject and/or remove a fluid from a subject. For example, the antimicrobial device may be utilized with one or more portions of fluid flow or fluid delivery systems such as, for example, an intravenous (IV) device that delivers substances (e.g., fluid) to and from one or more veins of a subject. Such IV devices may include a peripheral IV line having a cannula in communication with the vasculature of a subject. The IV device may include one or more connections, valves, and access ports for delivering fluids to and from the subject that may become contaminated while the IV device is connected to the subject (e.g., in fluid communication with one or more portions of subject's internal systems). For example, the peripheral IV line may include one or more of needle injection sites (e.g., y-sites), needleless injection sites (e.g., a luer-activated valve (LAV)), and other fluid transfer devices. Accordingly, antimicrobial devices as disclosed herein may be utilized with any such connectors, valves, and access ports in such fluid flow or fluid delivery systems.

The antimicrobial devices disclosed herein may be particularly useful in at least temporarily (e.g., transiently, for a selected period a time) connecting to (e.g., coupling and retaining) one or more portions of a medical device, such as, the various portions of fluid systems discussed above in order to disinfect and/or protect portions of the medical device that are exposed to potential contamination during use (e.g., during use with a subject). For example, the antimicrobial device may disinfect and protect a portion of the medical device from further contamination as the antimicrobial device remains secured to the medical device in disinfecting contact with the portion of the medical device.

Such antimicrobial devices are typically configured to connect and secure to both a portion of a medical device lacking a threaded connection (i.e., non-threaded) and/or a portion of a medical including threaded connection (e.g., threads of a Luer connection). In other words, the antimicrobial device may connect and secure to a portion of medical device with or without a threaded connection. For example, as discussed below in greater detail, the antimicrobial device includes one or more flexible portions (e.g., at least a portion of a housing of the antimicrobial device) configured to engage with a portion of a non-threaded (e.g., having a smooth surface, a flat surface, an uneven non-threaded surface, or combinations thereof) access port of a medical device (e.g., a needle injection site of an IV device). The one or more flexible portions of the antimicrobial device may also engage with a portion of a threaded portion (e.g., threads of Luer connection) of an access port of a medical device (e.g., a needleless injection site of an IV device). In some embodiments, the one or more flexible portions alone engage and secure the threaded portion (e.g., the threads) of the medical device to retain the portion of the medical device within a housing of the antimicrobial device without the need for a set of complementary threads on the housing.

In some embodiments, the one or more flexible portions of the antimicrobial device are formed as flexible members (e.g., flexible protrusions of the housing) extending inwardly in a cavity of the antimicrobial device. For example, such flexible protrusions of the housing may act to engage with and retain a portion of a medical device inserted within the housing of the antimicrobial device. In some embodiments, the antimicrobial device only includes flexible protrusions in order to engage with a medical device (e.g., the antimicrobial device may lack threads within the antimicrobial device).

In some embodiments, the housing of the antimicrobial device is formed from a flexible material. For example, the flexible housing may act to engage with and retain a portion of a medical device inserted within the housing of the antimicrobial device. In some embodiments, such a flexible housing is utilized in addition to or in place of the flexible protrusions. In other words, the one or more flexible portions of the housing of the antimicrobial device may include one or both of a flexible housing and one or more flexible protrusions.

In some embodiments, the flexible portions of the housing of the antimicrobial device are flexible in the sense that the flexible portions (e.g., the protrusions and the flexible housing) are easily deformable by a medical practitioner as the practitioner installs and removes the antimicrobial device from the portion of the medical device by hand. The stiffness of the flexible portions may be selected based on the configuration of the flexible portions of the antimicrobial device such that the flexible portions may be deformed (e.g., elastically deformed) by the user (e.g., using only force applied directly by the user without the use of any external tools, machines, or other devices) in order to engage and retain the antimicrobial device on the portion of the medical device.

Such antimicrobial devices including one or more flexible portions may be relatively more robust than a threaded cap having a disinfectant therein as such threaded caps are generally limited to connecting only with one particular type of a complementary threaded portion of a medical device. Further, the threading protruding from an inner surface within the threaded cap limits the size (e.g., diameter) of the portions of the medical device that may be received within the threaded cap.

Figure 1:
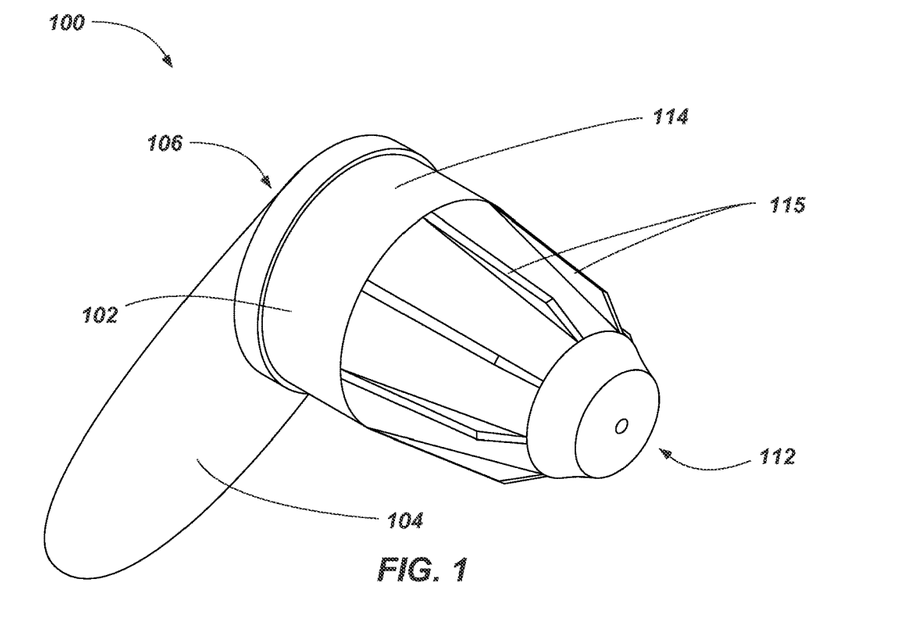
FIG. 1 illustrates a perspective view of a device in accordance with an embodiment of the disclosure.

FIG. 1 illustrates a perspective view of a device 100 (e.g., an antimicrobial device). As shown in FIG. 1, the antimicrobial device 100 includes a housing (e.g., flexible housing 102) formed as cap and a sealing member 104. The housing 102 includes a first open end (e.g., proximal end 106) forming an access port 108 (FIG. 2) in the antimicrobial device to a cavity 110 (FIG. 2) formed in the housing 102 for receiving at least portion of a medical device within the antimicrobial device 100. The housing 102 further includes a second closed end (e.g., distal end 112) opposing the proximal end 106.

The sealing member 104 may comprise any suitable nonporous material configured to at least partially seal a volume of fluid within the flexible housing 102 of the antimicrobial device 100. For example, the sealing member 104 may have a pull-tab configuration (e.g., a metal tab formed from a foil, polymer tab, etc.) having a first portion sealed about the flexible housing 102 and a second portion for a practitioner to grab in order to remove the sealing member 104.

In some embodiments, outer surface 114 of the flexible housing 102 includes one or more ribs 115 positioned about (e.g., around) the housing 102 and extending along the housing 102 (e.g., along a longitudinal axis 124 of the flexible housing 102 (FIG. 2)). Such ribs 115 may assist a practitioner or user in gripping and manipulating the antimicrobial device 100 during use.

As mentioned above, in some embodiments, the housing 102 is formed to be flexible (e.g., formed from a flexible material). For example, the flexible housing 102 is flexible in the sense that the flexible housing 102 is easily deformable by a health care provider as he or she installs and removes the antimicrobial device 100 from the portion of the medical device by hand. In some embodiments, the flexible housing 102 is flexible in the sense that the practitioner or other user can elastically deform the flexible housing 102 (e.g., the sidewalls of the flexible housing 102) by applying a force to the flexible housing 102 with only the practitioner's fingers. For example, the practitioner may compress (e.g., collapse) the flexible housing 102 by applying a force to the flexible housing 102 between the practitioner's fingers (e.g., pinching, squeezing, etc.). Such a flexible housing 102 may be formed from one or more polymers, such as, for example, a thermoplastic polyurethane (e.g., ELASTOLLAN® available from BASF Corporation of Wyandotte, Mich.).

In some embodiments, the flexible housing 102 is formed (e.g., entirely formed) from a flexible material having a relatively low durometer indicating the relatively low hardness of the material as compared to other relatively stiffer (e.g., rigid) polymers or other types of materials. For example, the flexible housing 102 may be formed from a material having a type A Shore hardness of less than 100 (e.g., less than 90, less than 80, less than 70, less than 60). In some embodiments, the flexible housing 102 is formed from a material having a type A Shore hardness between 50 and 100 (e.g., 60 to 90, 70 to 90).

In some embodiments, the flexible housing 102 is formed (e.g., entirely formed) from a material having a relatively low Young's modulus (e.g., tensile modulus or elastic modulus) indicating the relatively low stiffness of the material as compared to other relatively harder (e.g., rigid) polymers or other types of materials. For example, the flexible housing 102 may be formed from a material having a Young's modulus of less than 100 MPa (e.g., less than 50 MPa, less than 40 MPa, less than 30 MPa, less than 20 MPa, less than 10 MPa). In some embodiments, the flexible housing 102 is formed from a material having a Young's modulus between 0.1 MPa and 100 MPa (e.g., 10 MPa to 20 MPa, 5 MPa to 50 MPa, 1 MPa to 20 MPa).

In some embodiments, a portion (e.g., a majority, an entirety, the sidewalls extending along the longitudinal axis 122) of the flexible housing 102 has a wall thickness of between 1.0 mm and 4.0 mm (e.g., 1.0 mm to 2.0 mm, 1.2 mm to 1.6 mm, about 1.5 mm).

Figure 2:
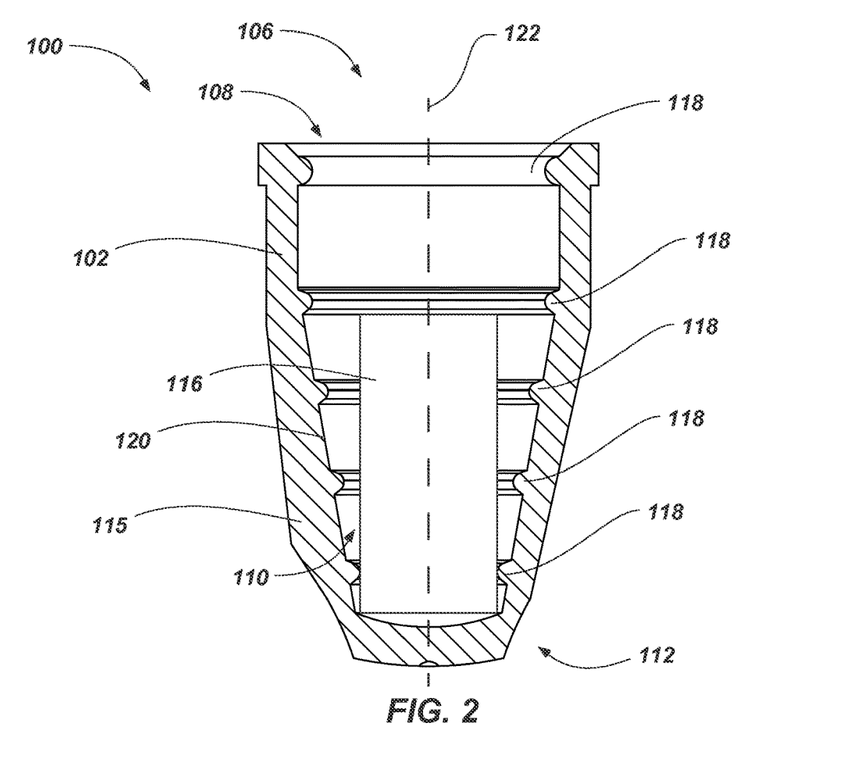
FIG. 2 illustrates a partial cross-sectional side view of the device shown in FIG. 1.

FIG. 2 illustrates a partial cross-sectional side view of the antimicrobial device 100. As shown in FIG. 2, the antimicrobial device 100 includes a volume of antimicrobial substance 116 within the flexible housing 102. As discussed above, the antimicrobial substance 116 may comprise at least one of a disinfectant and antiseptic in a fluid state at various concentrations. The volume of antimicrobial substance 116 will typically include a pad (e.g., sponge material, such as an open-cell foam, felt, fiber matrix, combinations thereof, etc.) configured to retain the antimicrobial substance within the flexible housing 102. The pad of the volume of antimicrobial substance 116 may be at least partially compressible such that the volume of antimicrobial substance 116 may fit within the flexible housing 102 (e.g., positioned proximate a distal end 112 of the flexible housing 102) and may at least partially contact (e.g., surround) a portion of a medical device when received within the flexible housing 102. For example, the pad of the volume of antimicrobial substance 116 may at least partially deform to receive the portion of the medical device inserted into the flexible housing 102 (see, e.g., FIGS. 3 and 4).

The housing 102 of the antimicrobial device 100 may include one or more protrusions 118 (e.g., one or more flexible protrusions) extending about (e.g., around an entirety of) an inner surface 120 of the housing 102 and extending inwardly into the cavity 110 from the inner surface 120 of the housing 102 in a direction transverse to (e.g., perpendicular to) the longitudinal axis 122 of the housing 102. For example, the flexible protrusions 118 may extend around the inner surface 120 of the housing 102 and may surround (e.g., encompass, bound) a portion of the cavity 110. In some embodiments, the flexible protrusions 118 extend around the inner surface 120 of the housing 102 at a constant radius from a single point on the longitudinal axis.

Such flexible protrusions 118 may be configured to at least partially yield (e.g., elastically yield) about a portion of a medical device when inserted within the flexible housing 102. For example, the flexible protrusions 118 may be formed with similar or the same materials discussed above in relation to the flexible housing 102 and may include similar or the same value of type A Shore hardness and/or Young's modulus.

In some embodiments, the flexible housing 102 and the flexible protrusions 118 are formed (e.g., injection molded) as a single, unitary (e.g., monolithic) structure. For example, integral portions of the flexible housing 102 extending inwardly may form the flexible protrusions 118. In other embodiments, the protrusions 118 are separate from the housing 102 and are coupled or otherwise secured to the flexible housing 102.

As depicted, at least one protrusion 118 of the antimicrobial device 100 may be positioned proximate to (e.g., at) the proximal end 106 of the flexible housing 102 (e.g., at access port 108). In some embodiments, the antimicrobial device 100 (e.g., the flexible housing 102) includes a plurality of protrusions 118 positioned along a longitudinal axis 122 (e.g., centerline) of the flexible housing 102. For example, each protrusion 118 may be formed as a ring (e.g., circles) having a center positioned along the longitudinal axis 122 of the flexible housing 102. Thus, the protrusions 118 may be a series of concentric or coaxial rings positioned along the longitudinal axis 122 of the flexible housing 102. As depicted, each ring of the protrusions 118 may have a static (e.g., constant, nonmoving) center point that does not vary along longitudinal axis 122 of the flexible housing 102 (e.g., as compared to threads, which have a helical structure).

In some embodiments, the flexible housing 102 is formed to exhibit a tapered shape (e.g., a frustoconical shape). For example, the inner surface 120 of the housing 102 may be tapered where the cavity 110 at the proximal end 106 of the housing 102 has a relatively larger area or volume and the cavity 110 at the distal end 112 of the housing 102 has a relatively smaller area or volume (e.g., the housing 102 at the distal end 112 has a diameter smaller than a diameter of the housing 102 at the proximal end 106). As depicted, in such an embodiment, the size (e.g., diameter) of the protrusions 118 may also become smaller along the longitudinal axis 122 of the flexible housing 102 due to the tapering of the flexible housing 102. Such a taper may enable the antimicrobial device 100 to be used with and secure to medical devices of numerous sizes by enabling the medical device to be advanced into the flexible housing 102 until the medical device contacts one or more of the flexible protrusions 118 and/or housing 102.

Figure 3:
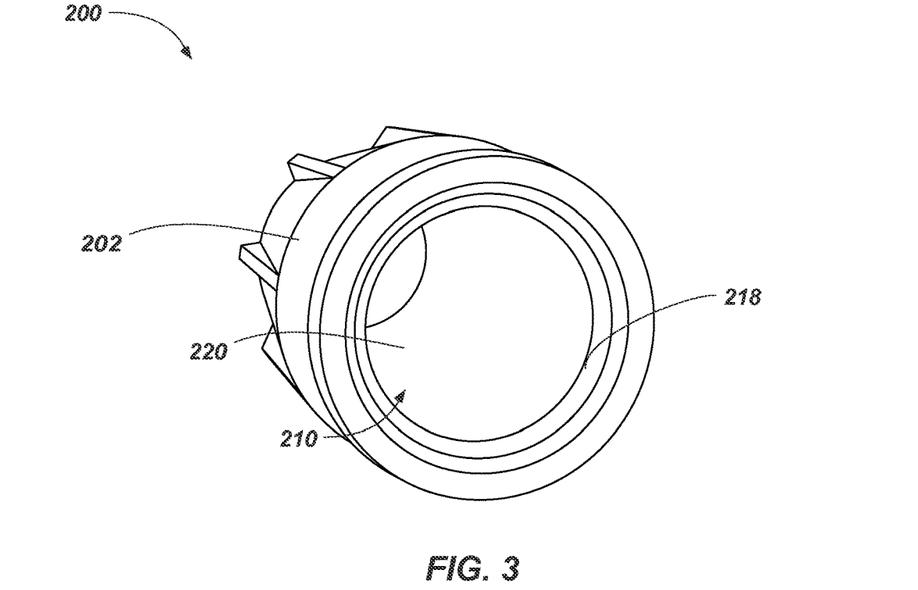
FIG. 3 illustrates a perspective view of a device in accordance with an embodiment of the disclosure.
Figure 4:
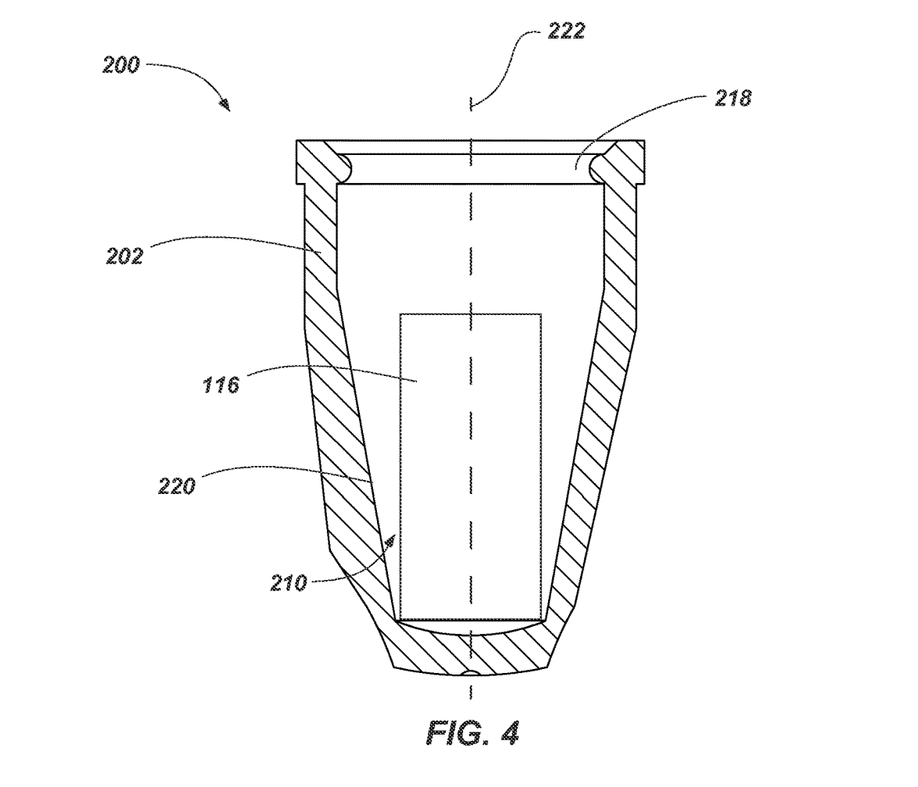
FIG. 4 illustrates a partial cross-sectional side view of the device shown in FIG. 2.

FIGS. 3 and 4 illustrate a perspective view of a device 200 (e.g., an antimicrobial device 200) and a partial cross-sectional side view of the device 200, respectively, that may be the same or somewhat similar to and may include one or more features of the antimicrobial device 100 discussed above with regard to FIGS. 1 and 2. As shown in FIGS. 3 and 4, the antimicrobial device 200 includes a housing 202 (e.g., a flexible housing similar to flexible housing 202 discussed above) having the volume of antimicrobial substance 116 disposed within the housing 202. The housing 202 includes one protrusion 218 (e.g., a flexible protrusion) extending inwardly into the cavity 210 from an inner surface 220 of the housing 202. As above, such a flexible protrusion 218 may be configured to at least partially yield (e.g., elastically yield) about a portion of a medical device when inserted within the flexible housing 202.

The remainder of the inner surface 220 of the housing 202 of the antimicrobial device 200 may have be substantially smooth inner surface 126. In other words, the housing 202 of the antimicrobial device 200 may lack threads such that the inner surface 220 extending along the longitudinal axis 222 (e.g., centerline) of the housing 202 is substantially smooth and unencumbered for receiving one or more portions of a medical device (e.g., portions of varying sizes, portion lacking threading, or combinations thereof).

In some embodiments, the flexible housing 202 (e.g., alone or in unison with the flexible protrusion 218) is utilized to retain the portion of the medical device. For example, the inner surface 220 of the housing 202 may deform about the portion of the medical device due to contact with the portion of the medical device (e.g., may stretch around the portion of the medical device) in order to retain the medical device in the housing 202.

Figure 5:
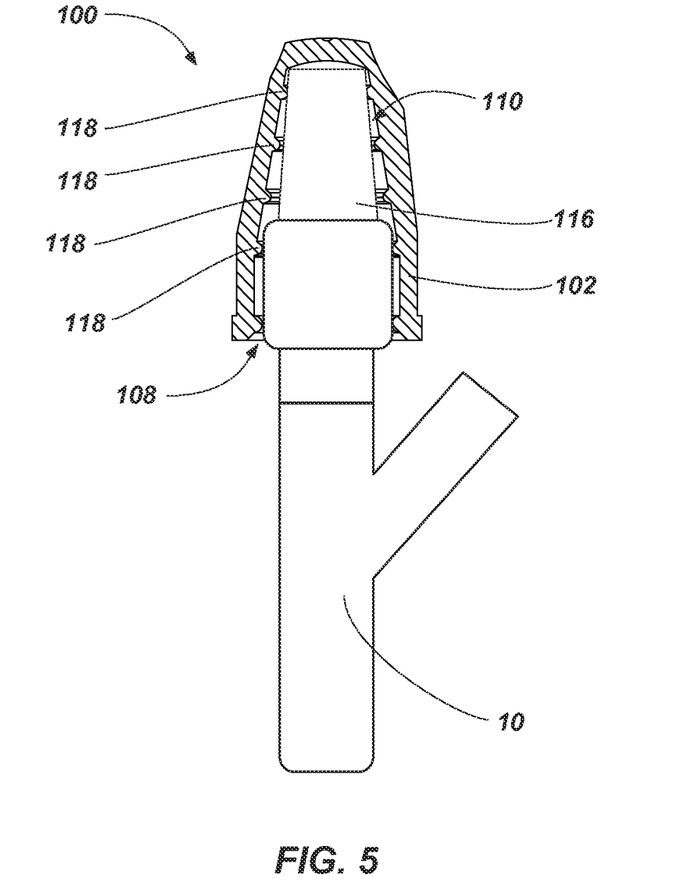
FIG. 5 illustrates a partial cross-sectional side view of an antimicrobial device such as, for example, the device shown in FIGS. 1 and 2 received on a portion of a medical device.

FIG. 5 illustrates a partial cross-sectional side view of an antimicrobial device such as, for example, the antimicrobial device 100 shown in FIGS. 1 and 2 received on a portion of a medical device 10. As shown in FIG. 5, the portion of the medical device 10 (e.g., a non-threaded portion of a needle access site) may be inserted through the access port 108 of the flexible housing 102. For example, the portion of the medical device 10 may be forced through the access port 108 to elastically deform at least a portion of one or more the protrusions 118 and the flexible housing 102.

The portion of the medical device 10 may be inserted into the flexible housing 102 in order to at least partially disinfect the portion of the medical device 10 with the volume of antimicrobial substance 116. In some embodiments, the portion of the medical device 10 at least partially deforms the volume of antimicrobial substance 116 (e.g., the pad holding the volume of antimicrobial substance 116).

In some embodiments, one or more of the protrusions 118 and/or the flexible housing 102 will act to secure the portion of the medical device 10 within the flexible housing 102. For example, the opening 112 may be sized such that the protrusions 118 and/or the flexible housing 102 are deformed (e.g., elastically deformed) in order to insert or remove the portion of the medical device 10. In other words, a cross-sectional area (e.g., diameter) of one or more the protrusions 118 and/or the flexible housing 102 is enlarged by the medical device 10 as the medical device 10 is inserted within the housing 102. Accordingly, the portion of the medical device 10 may be retained in the flexible housing 102 until enough force is applied to remove the portion of the medical device 10 from the flexible housing 102. In some embodiments, the protrusions 118 are sized such that the inner portion of the protrusions 118 surrounding the access port 108 and cavity 110 may contact a portion of the medical device 10 such that friction between the portion of the medical device 10 and the inner portion of the protrusions 118 acts to retain the portion of the medical device 10 within the flexible housing 102.

Figure 6:
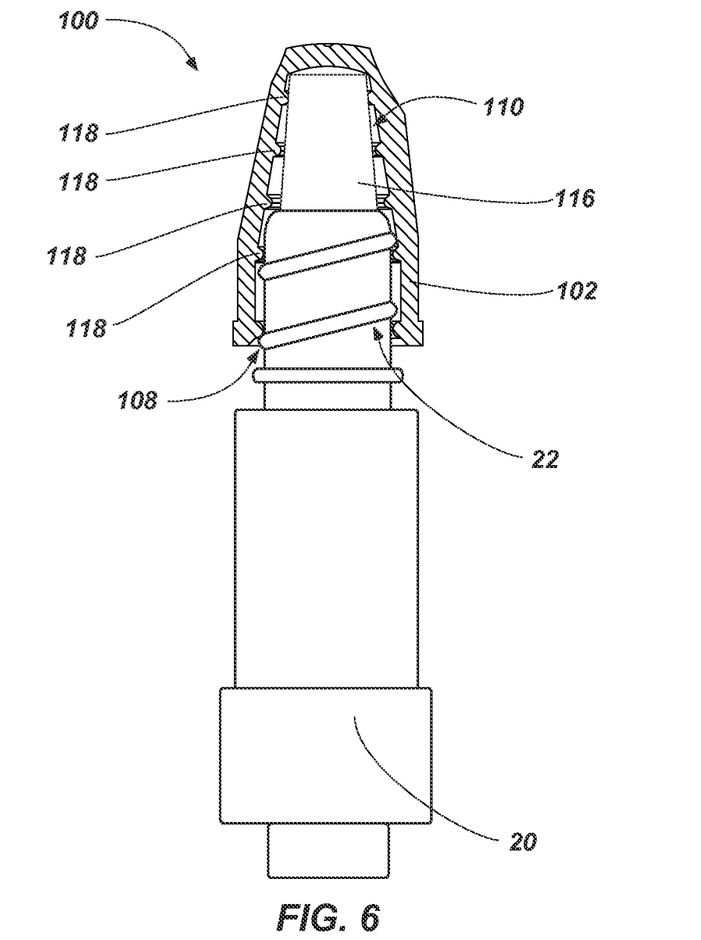
FIG. 6 illustrates a partial cross-sectional side view of an antimicrobial device such as, for example, the device shown in FIGS. 1 and 2 received on a portion of another medical device.

FIG. 6 illustrates a partial cross-sectional side view of an antimicrobial device such as, for example, the antimicrobial device 100 shown in FIGS. 1 and 2 received on a threaded portion 22 of a medical device 20. As shown in FIG. 6, the threaded portion 22 of the medical device 20 (e.g., a threaded Luer connection of a needleless access site) may be inserted through the access port 108 of the flexible housing 102. For example, the threaded portion 22 of the medical device 20 may be forced through the access port 108 to elastically deform at least a portion of one or more the protrusions 118 and/or the flexible housing 102.

The threaded portion 22 of the medical device 20 may be inserted into the flexible housing 102 in order to at least partially disinfect the threaded portion 22 of the medical device 20 with the volume of antimicrobial substance 116. In some embodiments, the threaded portion 22 of the medical device 10 at least partially deforms the volume of antimicrobial substance 116 (e.g., the pad holding the volume of antimicrobial substance 116).

In some embodiments, one or more of the protrusions 118 and/or the flexible housing 102 will act to secure the threaded portion 22 of the medical device 20 within the flexible housing 102. For example, the opening 112 may be sized such that the protrusions 118 and/or the flexible housing 102 are elastically deformed in order to insert or remove the threaded portion 22 of the medical device 20. In other words, a cross-sectional area (e.g., diameter) of one or more the protrusions 118 and/or the flexible housing 102 is enlarged by the threaded portion 22 of the medical device 20 as the medical device 20 is inserted within the housing 102. Accordingly, the threaded portion 22 of the medical device 20 may be retained in the flexible housing 102 until enough force is applied to remove the threaded portion 22 of the medical device 20 from the flexible housing 102. In some embodiments, the protrusions 118 are sized such that the inner portion of the protrusions 118 surrounding the access port 108 and cavity 110 may contact the threaded portion 22 of the medical device 20 such that friction between the threaded portion 22 of the medical device 20 and the inner portion of the protrusions 118 acts to the threaded portion 22 of the medical device 20 within the flexible housing 102.

Accordingly, as discussed herein, one or more flexible portions (e.g., the one or more protrusions 118, 218 and/or the flexible housing 102, 202) may enable the antimicrobial device 100, 200 to be retained on a non-threaded portion of a medical device such as, for example, a needle access site, a threaded portion of a medical device such as, for example, a needleless access site, or combinations thereof.

In some embodiments, in addition to the materials discussed above, the antimicrobial device is formed with one or more suitable materials such as, for example, metals, alloys, other polymers, silicones, elastomers, ceramics, combinations thereof, etc.

Once being apprised of the instant antimicrobial devices, one of ordinary skill in the art will be readily able to make (e.g., by injection molding) and assemble the device.

What is claimed is:

1. An antimicrobial device for use in disinfecting at least a portion of a medical device, the antimicrobial device comprising:

a monolithic, nonporous flexible housing formed from a flexible material, the flexible housing having a first open end forming an access port in the antimicrobial device to a cavity formed in the flexible housing for receiving the at least portion of the medical device within the antimicrobial device, a second closed end opposing the first open end, and a longitudinal axis extending between the first open end and the second closed end, the first open end being defined by a furthest longitudinal extent of the housing at a first longitudinal end of the housing, wherein the cavity in the flexible housing and an outer surface of the flexible housing are both tapered along the longitudinal axis of the flexible housing;

an antimicrobial substance contained within the cavity in an amount sufficient to disinfect at least a portion of the medical device;

a plurality of flexible concentric protrusions, at least one flexible protrusion of the plurality of flexible protrusions positioned at and directly adjacent to the first open end and extending around and into the cavity from an inner surface of the flexible housing in a direction perpendicular to the longitudinal axis of the flexible housing, wherein the at least one flexible protrusion is configured to directly engage with and secure the antimicrobial device to the at least a portion of the medical device in a manner allowing for the antimicrobial substance to make surface contact with the at least a portion of the medical device, wherein each successive concentric protrusion of the plurality of flexible concentric protrusions has a diameter that is less than a diameter of an adjacent concentric protrusion of the plurality of flexible concentric protrusions, wherein the at least one flexible protrusion and the flexible housing comprise a single unitary structure formed by injection molding; and a nonporous sealing member adhered to the first open end, the sealing member and the nonporous flexible housing configured to entirely contain the antimicrobial substance within the cavity, while only enabling the antimicrobial substance to pass through the access port at the first open end after the nonporous sealing member has been removed from the housing.

2. The antimicrobial device of claim 1, wherein the at least one flexible protrusion encompasses the cavity.

3. The antimicrobial device of claim 1, wherein the at least one flexible protrusion is further configured to secure the antimicrobial substance to a threaded portion of a medical device and a non-threaded portion of a medical device.

4. The antimicrobial device of claim 1, wherein the at least one flexible protrusion comprises a plurality of flexible protrusions positioned along the longitudinal axis of the flexible housing.

5. The antimicrobial device of claim 1, wherein the cavity in the flexible housing and the outer surface exhibit a non-tapered portion along the longitudinal axis of the flexible housing at a location proximate the first open end.

6. The antimicrobial device of claim 1, wherein the flexible housing is configured to engage with both a needle access site and a needleless access site.

7. The antimicrobial device of claim 1, wherein the flexible housing does not have threads formed on an inner surface of the flexible housing.

8. The antimicrobial device of claim 1, wherein the flexible housing is configured to elastically deform responsive to a force applied to the flexible housing by fingers of a user.

9. The antimicrobial device of claim 1, wherein at least one of the flexible housing and the at least one flexible protrusion are configured to elastically deform about the at least a portion of the medical device in order to secure the antimicrobial device to the at least a portion of the medical device.

10. The antimicrobial device of claim 1, wherein the flexible housing is entirely formed from the flexible material exhibiting at least one of a type A Shore hardness of less than 90 and a Young's modulus of less than 50 MPa.

11. The antimicrobial device of claim 1, wherein only the at least one flexible protrusion is configured to secure the antimicrobial device to the at least a portion of the medical device.

12. The antimicrobial device of claim 1, further comprising a plurality of external ribs extending from the outer surface of the flexible housing along the longitudinal axis of the flexible housing.

13. The antimicrobial device of claim 1, wherein the flexible housing comprises:

a tapered portion wherein the cavity in the flexible housing and the outer surface of the flexible housing are both tapered along the longitudinal axis of the flexible housing; and a non-tapered portion adjacent the tapered portion and the first open end wherein the cavity in the flexible housing and the outer surface of the flexible housing exhibit a substantially constant cross section along the longitudinal axis of the flexible housing.

14. The antimicrobial device of claim 1, wherein the flexible housing further comprises a non-tapered portion adjacent the tapered portion and the first open end wherein the cavity in the flexible housing and the outer surface of the flexible housing exhibit a substantially constant cross section along the longitudinal axis of the flexible housing.

15. A medical device assembly comprising:

a device access port configured to at least one of sample fluid from a subject and deliver fluid to a subject; and the antimicrobial device of claim 1 adapted to disinfect at least a portion of the access port.

16. A method of disinfecting a portion of a device, the method comprising:

deforming the flexible housing of the antimicrobial device of claim 1;

retaining the antimicrobial device on the portion of the device for a selected period of time with the at least one flexible protrusion of the plurality of flexible protrusions so as to disinfect the portion of the device; and removing the antimicrobial device from the portion of the device.

17. The method according to claim 16, wherein deforming at least a portion of a housing of the antimicrobial device comprises elastically deforming the housing of the antimicrobial device comprising a flexible material with a force applied to the flexible housing with fingers of a user.

18. The method according to claim 16, further comprising retaining the antimicrobial device on the portion of the device with only the at least one protrusion of the plurality of protrusions.

19. The method according to claim 16, further comprising engaging a threaded portion of the device with the housing of the antimicrobial device.

20. The method according to claim 16, further comprising engaging a non-threaded portion of the device with the housing of the antimicrobial device.

* * * * *

UNITED STATES PATENT AND TRADEMARK OFFICE
CERTIFICATE OF CORRECTION

PATENT NO. : 10,245,342 B2
APPLICATION NO. : 14/559746
DATED : April 2, 2019
INVENTOR(S) : Li Min She et al.

It is certified that error appears in the above-identified patent and that said Letters Patent is hereby corrected as shown below:

On the Title Page

In ITEM (72) Inventors:   change "Li Min She, Guangdong (CN)"
to --Li Min She, Foshan (CN);--

In the Specification

| | | |
|---|---|---|
| Column 8, | Line 48, | change "have be substantially" to --have a substantially-- |
| Column 8, | Line 49, | change "surface 126." to --surface 220.-- |
| Column 9, | Line 17, | change "the opening" to --the access port or opening-- |
| Column 9, | Line 57, | change "the opening" to --the access port or opening-- |

Signed and Sealed this
Fourteenth Day of May, 2019

Andrei Iancu
*Director of the United States Patent and Trademark Office*